(12) United States Patent
Alheidt et al.

(10) Patent No.: US 9,597,126 B2
(45) Date of Patent: Mar. 21, 2017

(54) DISTRACTION/COMPRESSION POSTERIOR ROD SYSTEM AND METHODS OF USE

(71) Applicant: Stryker European Holdings I, LLC, Kalamazoo, MI (US)

(72) Inventors: Thomas A. Alheidt, Sussex, NJ (US); Christine Herrmann, Fair Lawn, NJ (US); Bryan D. Milz, Florida, NY (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 0 days.

(21) Appl. No.: 14/949,289

(22) Filed: Nov. 23, 2015

(65) Prior Publication Data

US 2016/0074073 A1    Mar. 17, 2016

Related U.S. Application Data

(63) Continuation of application No. 13/792,810, filed on Mar. 11, 2013, now Pat. No. 9,220,605.

(51) Int. Cl.
*A61B 17/70*  (2006.01)
*A61F 2/44*  (2006.01)

(52) U.S. Cl.
CPC ...... *A61B 17/7077* (2013.01); *A61B 17/7001* (2013.01); *A61B 17/7002* (2013.01);
(Continued)

(58) Field of Classification Search
CPC . A61B 17/88; A61B 17/7067; A61B 17/7065; A61B 17/7062; A61F 2/4455; A61F 2002/4415
See application file for complete search history.

(56) References Cited

U.S. PATENT DOCUMENTS 4,611,582 A     9/1986  Duff
4,733,657 A  *  3/1988  Kluger .................. A61B 17/66
                                                                    606/57
(Continued)

FOREIGN PATENT DOCUMENTS

DE      3841008 A1    6/1990
DE      9004960 U1    8/1991
(Continued)

OTHER PUBLICATIONS

Stryker Spine, Xia Anterior, Comprehensive Anatomical Implants, 2004.
(Continued)

*Primary Examiner* — Andrew Yang

(57) ABSTRACT

A method for fusing vertebral bodies comprising the steps of: mounting a first engagement member of a fixation member to a pedicle of a first vertebra and a second engagement member of the spinal fixation member to a pedicle of a second vertebra, the first engagement member having a first extension engaged with an expansion ring, the second engagement member having a second extension engaged with the expansion ring; inserting screws through the first and second engagement members and into the pedicles of the respective first and second vertebrae; rotating the expansion ring in a first direction, thereby distracting the first and second vertebrae; implanting an intervertebral implant between the first and second vertebrae after rotating the expansion ring in the first direction; and rotating the expansion ring in a second direction after implanting the intervertebral implant, thereby compressing the first and second vertebrae.

20 Claims, 9 Drawing Sheets

(52) U.S. Cl.
CPC ........ *A61B 17/707* (2013.01); *A61B 17/7014* (2013.01); *A61B 17/7062* (2013.01); *A61B 17/7067* (2013.01); *A61F 2/4455* (2013.01)

(56) References Cited

U.S. PATENT DOCUMENTS

| | | | |
|---|---|---|---|
| 5,468,241 | A | 11/1995 | Metz-Stavenhagen et al. |
| 6,126,660 | A | 10/2000 | Dietz |
| 6,530,929 | B1 * | 3/2003 | Justis ............... A61B 17/00234 606/103 |
| 7,578,822 | B2 * | 8/2009 | Rezach ............. A61B 17/7077 606/57 |
| 7,618,424 | B2 * | 11/2009 | Wilcox ............... A61B 17/025 606/105 |
| 8,308,802 | B2 | 11/2012 | Rhoda et al. |
| 8,372,081 | B1 * | 2/2013 | Schafer ............. A61B 17/7077 606/105 |
| 8,777,959 | B2 * | 7/2014 | Errico ................. A61B 17/025 606/99 |
| 8,801,758 | B2 * | 8/2014 | Milz .................... A61F 2/4603 606/279 |

FOREIGN PATENT DOCUMENTS

| | | |
|---|---|---|
| DE | 102007055745 A1 | 7/2008 |
| FR | 2919170 A1 | 1/2009 |
| WO | 2012044371 A1 | 4/2012 |

OTHER PUBLICATIONS

Stryker Spine, Xia 3 Spinal System, Surgical Technique, 2010.
Stryker Spine, THOR Tumor Trauma Plate, Operative Technique, 2008.
Extended European Search Report for Application No. EP14157873 dated Jun. 23, 2014.

* cited by examiner

DISTRACTION/COMPRESSION POSTERIOR ROD SYSTEM AND METHODS OF USE

CROSS-REFERENCE TO RELATED APPLICATIONS

This application is a continuation of U.S. application Ser. No. 13/792,810, filed on Mar. 11, 2013, the disclosure of which is incorporated herein by reference.

BACKGROUND OF THE INVENTION

The present invention relates to systems and methods for use in spinal surgery, and in particular, relates to an implant system that allows for distraction, compression and fixation of vertebral bodies.

An example of spinal surgery is spinal fusion. Spinal fusion is a procedure that may be a solution to severe or debilitating back pain, instability stemming from spinal disorders such as herniated or torn intervertebral discs, spondylolisthesis (e.g., where the vertebrae move out of position), or degenerative disc disease. Interbody fusion, specifically in the lumbar region, can be performed using a variety of approaches including posterior lumbar interbody fusion ("PLIF"), transforaminal lumbar interbody fusion ("TLIF"), lateral lumbar interbody fusion ("LLIF"), or anterior lumbar interbody fusion ("ALIF").

These lumbar interbody fusion procedures involve the removal of at least a portion of an intervertebral disc from the lumbar section of the spinal column, followed by fusion of the vertebrae that sit above and below the intervertebral disc. Typically, such fusion procedures involve the use of interbody implants (i.e., interbody fusion) and connected posterior structures. Fusion is achieved by distracting the vertebrae and inserting an intervertebral implant typically containing bone graft material into the space created by the removal of the intervertebral disc. Once the intervertebral implant is properly placed, the vertebrae may be compressed against it. Pedicle screws and rods may be used as an adjunct to interbody fusion to restrict the motion of the vertebrae while fusion takes place, to aid in setting the desired angle of lordosis, and to provide further fixation of the vertebrae.

Certain instruments exist that are used for distracting the vertebrae such as a pedicle or lamina distractors, for example. Other instruments exist that are used for compression of the vertebral bodies. Some instruments both distract and compress. However, these currently existing distraction and compression instruments are external instruments that are separate and apart from supplemental fixation devices, such as the above-noted pedicle screws and rods. Thus, multiple sets of instruments must be used for one procedure increasing the possibility of operating room confusion. Further, multiple instruments to achieve compression, distraction, and fixation increases the length of the interbody fusion procedure, which increases the probability for complications and may increase recovery time.

Therefore, there is a need for an internal fixation system that also acts as a distraction and compression device while utilizing only one set of instruments.

BRIEF SUMMARY OF THE INVENTION

According to a first embodiment of the present invention, a spinal fixation device is disclosed herein. The spinal fixation device includes a first engagement member. The first engagement member includes a first body and at least one extension. The first body includes a first aperture extending therethrough for receipt of a fastener. The at least one extension extends outwardly from the first body. The spinal fixation device further includes a second engagement member. The second engagement member includes a second body and at least one threaded extension. The at least one threaded extension extends outwardly from the second body, and the second body includes a second aperture extending therethrough for receipt of a fastener. Also included in the spinal fixation device, an expansion ring having a first end and a second end. The first end includes a threaded internal surface in threaded communication with the at least one threaded extension. The second end is rotatable with the at least one extension of the first engagement member such that a torque applied to the expansion ring moves the second engagement member with respect to the first engagement member.

Further, the at least one extension may include a first interlocking feature. Also, the second end of the expansion ring may include an internal surface that may include a second interlocking feature. The first interlocking feature and second interlocking feature may communicate rotatably. Additionally, the at least one extension of the first engagement member may be at least two arms elastically cantilevered to the first body. Also, the first interlocking feature of the at least one extension may be a flange, and the second interlocking feature may be a groove.

Continuing with this embodiment, a torque applied to the expansion ring may move the first and second engagement members towards and away from each other. Further, the spinal fixation device may include a driver. The driver may include a manipulation end and an engagement end. The engagement end may include a first array of teeth. Moreover, the second end of the expansion ring may include a second array of teeth configured to orthogonally engage the first array of teeth such that applying a torque to the manipulation end rotates the expansion ring, thereby moving the second engagement member with respect to the first engagement member.

Additionally, the spinal fixation device may include a plurality of pedicle engagement extensions extending from the first body and the second body. Further, at least one of the plurality of pedicle engagement extensions may include a window extending therethrough for viewing a pedicle bone. Even further, the first engagement member and second engagement member may include a plurality of serrations disposed between the plurality of pedicle engagement extensions.

The spinal fixation device may further include at least one first locking ring for locking a fastener. The at least one first locking ring may be disposed within the first aperture of the first engagement member. The spinal fixation device may also include at least one second locking ring that may be disposed within the second aperture of the second engagement member. The locking rings may be split rings. Additionally, the at least one threaded extension may be polyaxially mounted to the second engagement member.

According to another embodiment of the present invention, a spinal fixation device including a first screw capture member. The first screw capture member includes a first body and at least one extension. The first body includes a first aperture extending therethrough. The at least one extension extends outwardly from the first body. Also included in the spinal fixation devices is a second screw capture member. The second screw capture member includes a second body and at least one threaded extension, which extends outwardly from the body. The second body includes a second aperture extending therethrough. Additionally, the device includes a first pedicle engagement member. The first pedicle engagement member includes a first passageway extending therethrough and is rotatably mounted with the first screw capture member such that the first passageway of the first pedicle engagement member is in communication with the first aperture of the first screw capture member. Further included in the device, a second pedicle engagement member including a second passageway, which extends therethrough. The second pedicle engagement member is rotatably mounted to the second screw capture member such that the second passageway of the second pedicle engagement member is in communication with the second aperture of the second screw capture member. Also included in the spinal fixation device is an expansion ring. The expansion ring includes a first end and a second end. The first end includes a threaded internal surface, which is in threaded communication with the at least one threaded extension. The second end is in rotatable communication with the at least one extension of the first screw capture member. Where a torque is applied to the expansion ring, the second screw capture member and second pedicle engagement member move with respect to the first screw capture member and first pedicle engagement member.

Additionally, the at least one extension may include a first interlocking feature, and the second end of the expansion ring may include an internal surface. The internal surface may include a second interlocking feature such that the first interlocking feature and second interlocking feature may communicate rotatably. Further, the at least one extension of the first screw capture member may be at least two arms elastically cantilevered to the first body. Also, the first interlocking feature of the at least one extension may be a flange, and the second interlocking feature may be a groove. Moreover, where a torque may be applied to the expansion ring, the second screw capture member and second pedicle engagement member may move toward and away from the first screw capture member and first pedicle engagement member.

Continuing with this embodiment, the spinal fixation device may include a driver. The driver may include a manipulation end and an engagement end. The engagement end may have a first array of teeth. Further, the second end of the expansion ring may include a second array of teeth configured to orthogonally engage the first array of teeth. This configuration may be such that applying a torque to the manipulation end rotates the expansion ring, thereby moving the second screw capture member and second pedicle engagement member with respect to the first screw capture member and first pedicle engagement member. Moreover, the spinal fixation device may additionally include a plurality of pedicle engagement extensions. The plurality of pedicle engagement extensions may extend from the first and second pedicle engagement members.

Additionally, the at least one of the plurality of pedicle engagement extensions may include a window extending therethrough for viewing a pedicle bone. Further, the first and second pedicle engagement members may include a plurality of serrations disposed between the plurality of pedicle engagement extensions. Even further, the spinal fixation device may include at least one first locking ring and at least one second locking ring for locking a fastener. The at least one first locking ring may be disposed within the first passageway of the first pedicle engagement member. The at least one second locking ring may be disposed within the second passageway of the second pedicle engagement member. The locking rings may be split rings. Moreover, the at least one threaded extension may be polyaxially mounted to the second screw capture member.

In another embodiment of the present invention, a method for fusing vertebral bodies including a step of mounting a first engagement member of a fixation member to a pedicle of a first vertebra, and a second engagement member of the spinal fixation member to a pedicle of a second vertebra. The first engagement member includes a first extension engaged with an expansion ring. The second engagement member includes a second extension engaged with the expansion ring. The method further includes a step of inserting screws through the first and second engagement members and into the pedicles of the respective first and second vertebrae. Additionally, the method includes the step of rotating the expansion ring in a first direction, thereby distracting the first and second vertebrae. Further included is the step of rotating the expansion ring in a second direction, thereby compressing the first and second vertebrae.

Additionally, the method may include the step of implanting an intervertebral implant between the first and second vertebrae, whereby the step of rotating to distract occurs before implanting and the step to compress occurs after this step. Further, the method may include the steps of engaging the expansion ring with a tool and actuating the tool to rotate the expansion ring.

BRIEF DESCRIPTION OF THE DRAWINGS

These and other features, aspect, and advantages of the present invention will become better understood with regard to the following description, appended claims, and accompanying drawings where:

DETAILED DESCRIPTION

Figure 1:
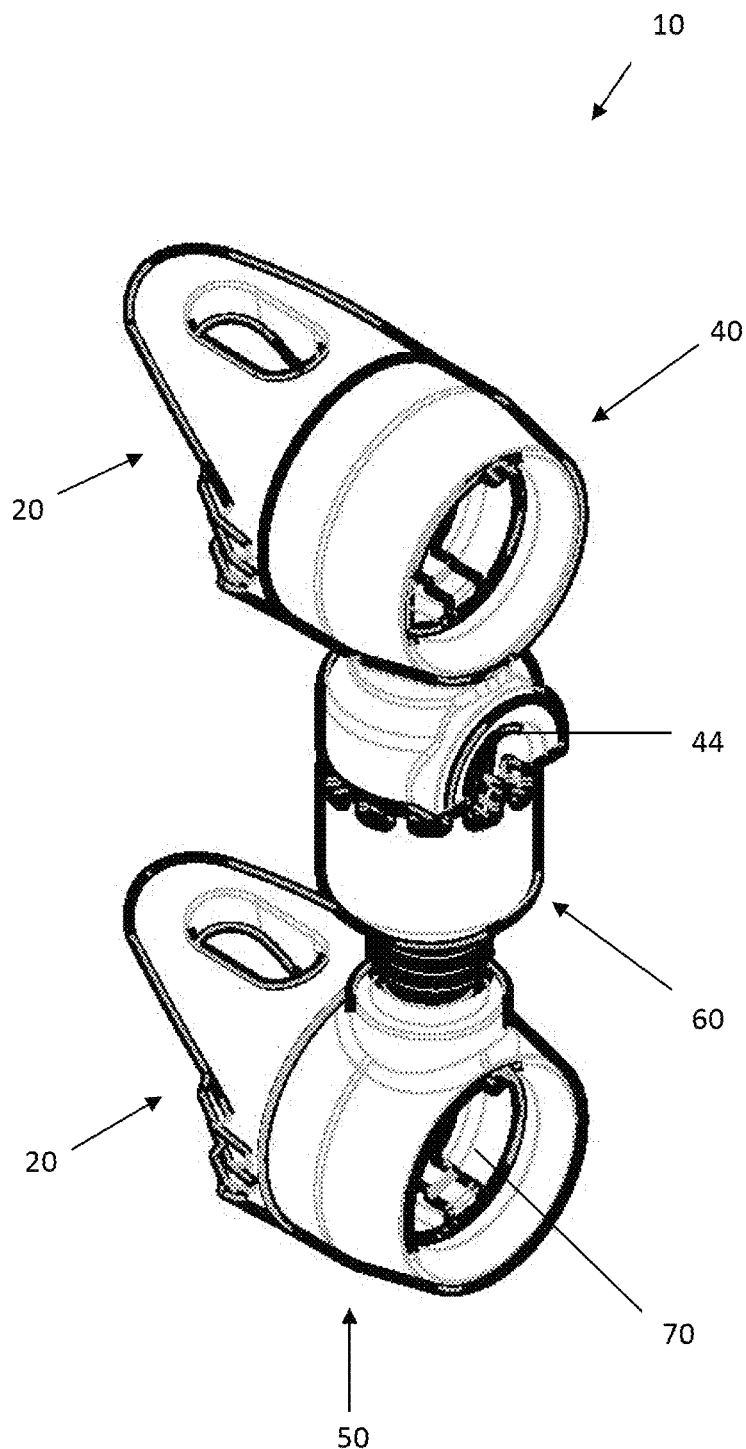
FIG. 1 is a front perspective view of a posterior fixation assembly.
Figure 2:
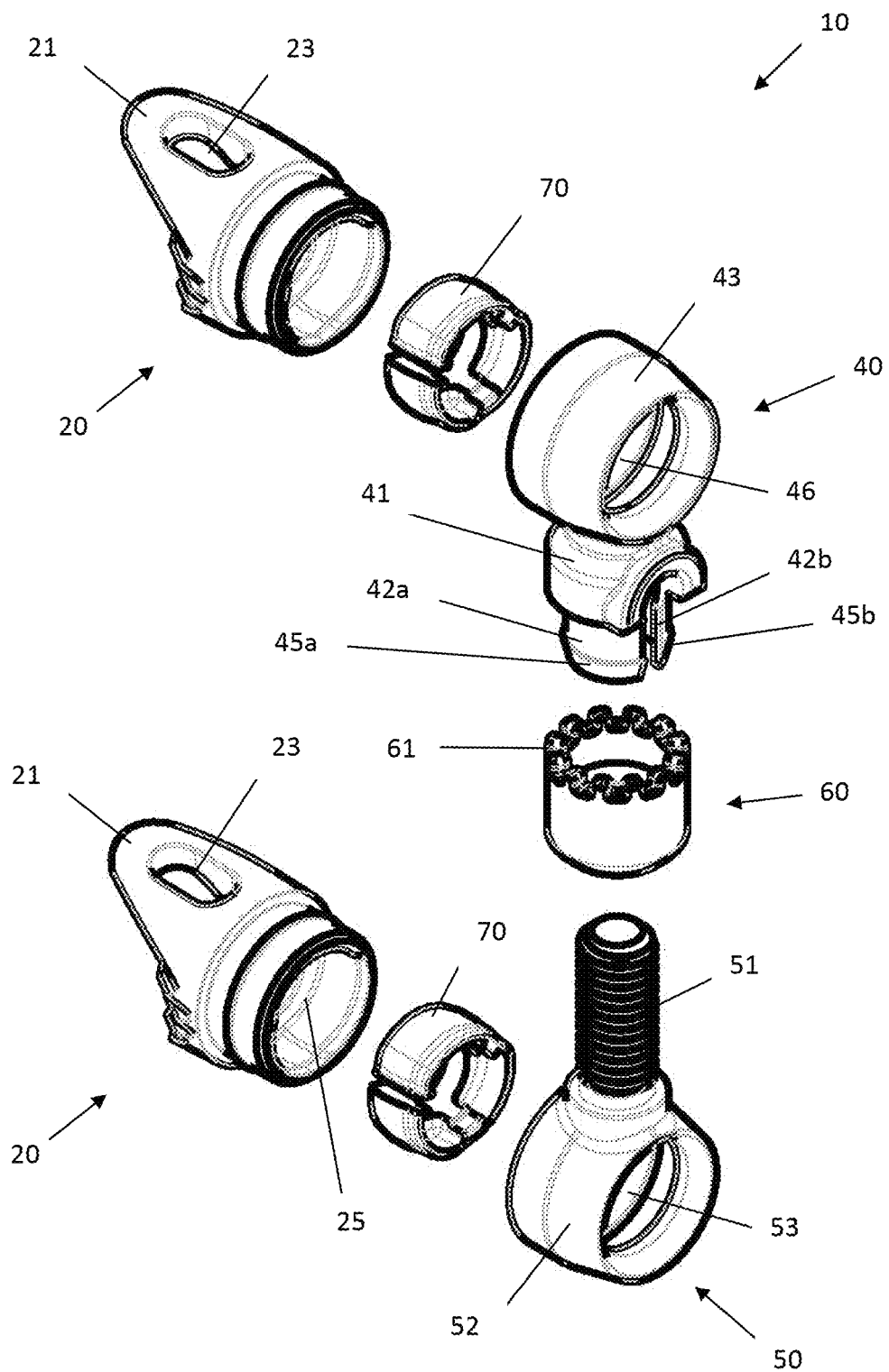
FIG. 2 is an exploded perspective view of the posterior fixation assembly of FIG. 1.
Figure 3:
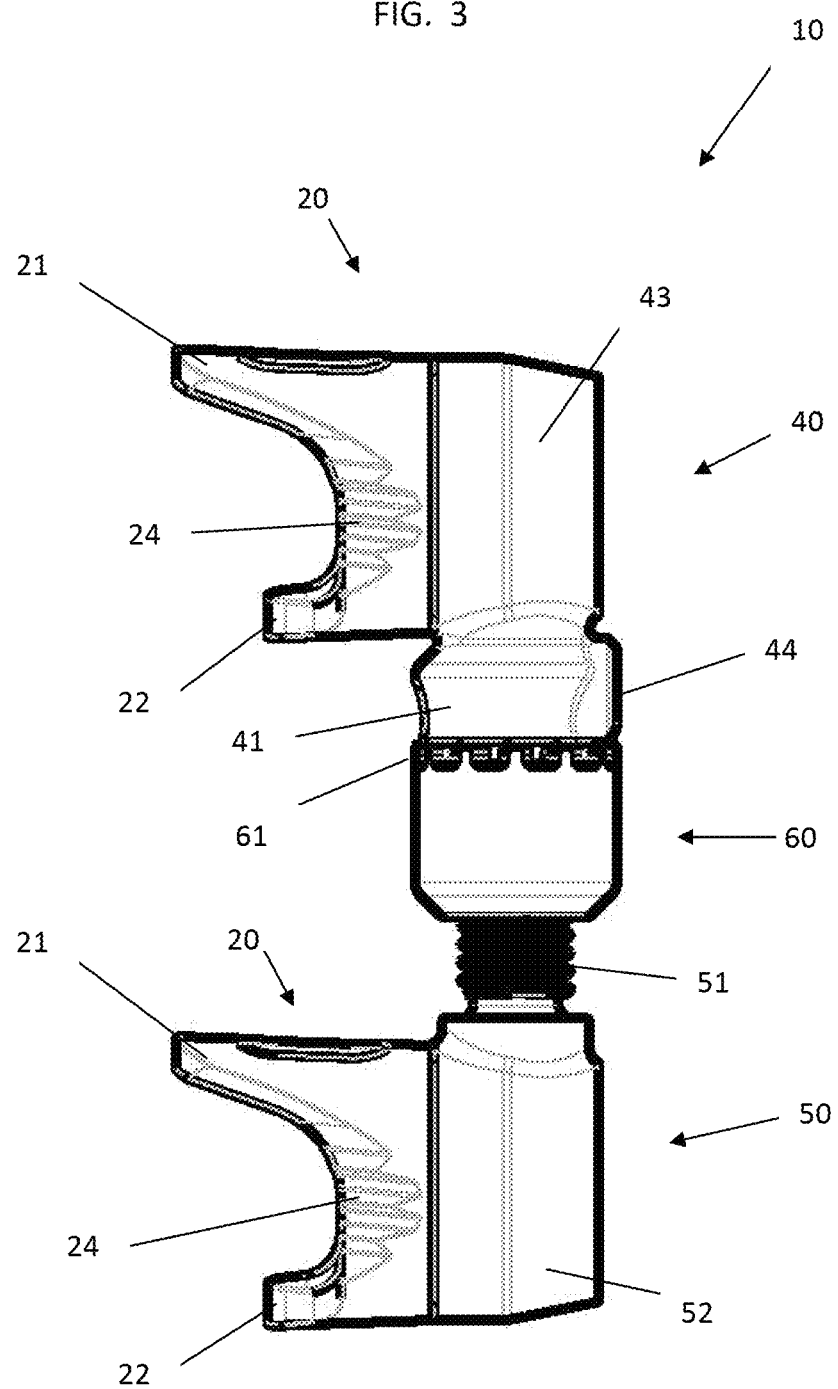
FIG. 3 is a side view of the posterior fixation assembly of FIG. 1.
Figure 4:
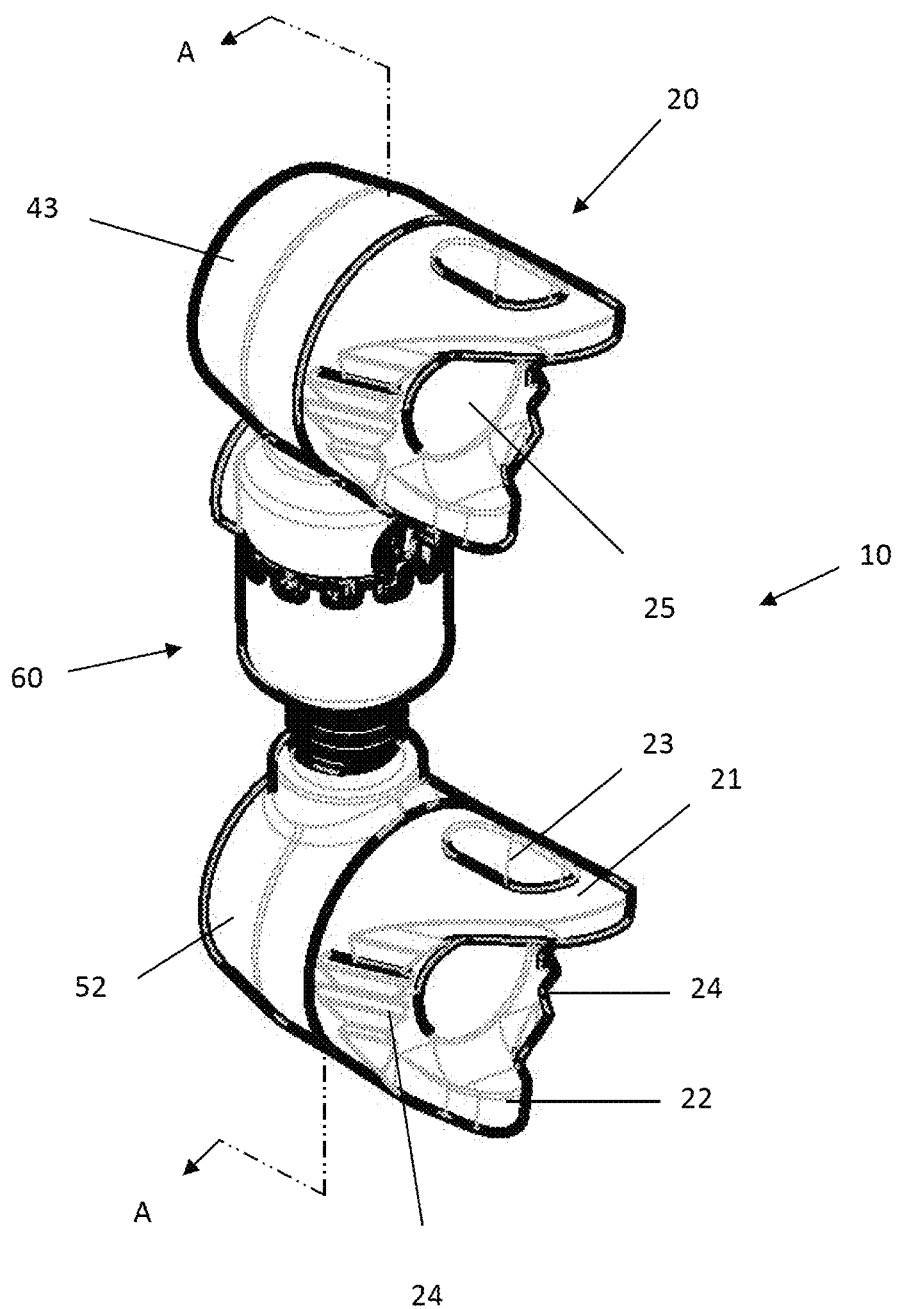
FIG. 4 is rear perspective view of the posterior fixation assembly of FIG. 1.

FIGS. 1-4 depict a posterior fixation assembly 10 in accordance with an embodiment of the present invention. The posterior fixation assembly 10 generally includes a first screw capture element 40, a second screw capture element 50, and an expansion ring 60. The posterior fixation assembly 10 may be made from any biocompatible material, such as titanium and stainless steel.

As shown, the first screw capture element 40 includes a cylindrical portion 43, a linking extension 41, and at least two spring arm extensions 42a, 42b. The cylindrical portion 43 has an internal passageway 46 for receiving a screw to allow connection to a portion of a vertebral body, such as a pedicle. The internal passageway 46 may also be adapted to rotatably receive a portion of a pedicle engagement device 20 as described below. The linking extension 41 extends outwardly from the cylindrical portion 43 and generally orthogonally with respect to the longitudinal axis thereof. The linking extension 41 may be an annulus-type structure with a hollow interior and a sidewall. The at least two spring arm extensions 42a, 42b may extend from the linking extension 41 and may be curved to receive a portion of the threaded extension 51 as described below. The spring arm extensions 42a, 42b are generally separated by a distance that allows for movement towards each other. One end of each of the spring arm extensions 42a, 42b may include a flange 45a, 45b. Further, the spring-arm extensions 42a, 42b may be tapered to facilitate connection to the expansion ring and to facilitated receipt of the threaded extension 51 as described below. In one embodiment, the spring arm extensions 42a, 42b and the linking extension 41 may be manufactured as a monolithic component, which cantilevers the spring arm extensions 42a, 42b with the linking extension 41. This cantilever feature and the spaces separating the spring arm extensions 42a, 42b allow the spring arm extensions 42a, 42b to have a spring-like action.

In one embodiment (not shown), the first screw capture element 40 may be configured for multilevel spinal fixation. In other words, the posterior fixation assembly 10 may be configured to allow for the distraction, compression, and fixation of more than a single level of vertebrae utilizing at least one interconnected device. In this embodiment, the first screw capture element 40 may include two linking extensions 41 extending outwardly from the cylindrical portion 43 generally in opposite directions from each other. Further, each linking extension 41 may include at least two spring arm extensions 42a, 42b extending from each linking extension 41. This configuration provides the operator flexibility in building the device 10 to accommodate the patient's needs.

The second screw capture element 50 generally includes a cylindrical portion 52 and a threaded extension 51. The cylindrical portion has an internal passageway 53 for receiving a screw to allow connection to a pedicle. The internal passageway 53 may be adapted to receive a portion of a pedicle engagement device 20 as described below. The threaded extension 51 extends outwardly from the cylindrical portion 52.

In one embodiment, the threaded portion 51 may extend orthogonally with respect to the longitudinal axis of the cylindrical portion. Another embodiment may include an overall system that may be provided with various options for the angle of the threaded extension 51. For example, a kit may be provided with several second screw capture elements 52 with threaded extensions 51 that are angled anywhere from 0 to 20 degrees with respect to the longitudinal axis of the cylindrical portion to provide a desired angle of lordosis when fully implanted. Further, this kit may include several first screw capture elements 40 that include one linking extension 41 and several first screw capture elements 40 that include two linking extensions 41. In another embodiment, the threaded extension 51 may be removably connected to the cylindrical portion allowing a polyaxial-type movement, for example a lockable ball and socket configuration. These multi-angle options provide the surgeon with flexibility in setting the desired angle of lordosis.

In another embodiment (not shown), the second screw capture element 50 may also be configured for multilevel spinal fixation. In this embodiment, the second screw capture element 50 may include two threaded extensions 51 extending outwardly from the cylindrical portion 52 generally in opposite directions from each other. Further, this embodiment may be provided with the multi-angle options provided the second screw capture element 52 that includes a single threaded extension 51 and may also be included in the kit, as described above. This configuration provides the operator flexibility in building the device to accommodate the patient's needs.

In a further embodiment (not shown), either or both of the first and second screw capture feature 40, 50 may have an offset feature. This offset feature may allow either the first or second screw capture feature 40, 50 to sit more anteriorly, medially, or laterally with respect to the other when fixed to the spine in order to more readily conform to the patient's anatomy.

Both the first screw capture element 40 and second screw capture element 50 may also include a pedicle engagement device 20. The pedicle engagement device 20 has an internal passageway 25 extending therethrough and may also include a long extension 21, a short extension 22, serrations 24 and a locking ring 70. The internal passageway 25 is generally cylindrical. However, a portion of the internal passageway 25 may have a non-uniform cross-section adapted to receive the locking ring 70. One end of the pedicle engagement devices 20 is configured to rotatably engage the first and second screw capture elements 40, 50 as described below. The long extension and short extension 21, 22 extend from the other end of the pedicle engagement device 20 and generally sit opposite each other forming a mouth-like structure for engaging a portion of a vertebra, such as a pedicle. The long extension 21 is configured to overlap and engage a portion of the superior side of a pedicle, while the short extension 22 is configured to overlap and engage a portion of the inferior side of the pedicle. The serrations 24 are disposed along the distance between the long and short extension for aiding in the fixed engagement with the vertebra. In one embodiment, the long extension 21 may include a window 23, which provides enhanced visibility to ensure the pedicle engagement devices 20 are properly seated onto the pedicle.

The pedicle engagement device 20 may have a different size and shape depending on the location along the spine the procedure is being performed. For example, the long and short extensions 21, 22 may be different sizes and lengths for L3 and L4 than for L5 and S1. Further, a system could include multiple geometric variations to provide substantial conformity to the patient population. Additionally, pedicle engagement devices 20 may even be customized to the individual patient's anatomy by using data collected from an MRI or CT scan.

The locking ring 70 is a ring that may be split at a portion along its circumference to provide for expansion and contraction. A series of grooves may be arranged along the internal surface of the ring for engagement with a torque applying device. As shown, the locking ring 70 is rotatably disposed within the internal passageway 25 of the pedicle engagement device 20 within the non-uniform cross-sectional portion. The non-uniformity of the cross-section allows for the locking ring 70 to contract as it is rotated, thereby closing the locking ring 70 and restricting its further rotation.

In one embodiment, a portion of the pedicle engagement devices 20 is disposed within the first and second screw capture elements 40, 50. This rotational ability of the pedicle engagement devices 20 facilitates optimal seating onto the pedicles. This rotatable connection may be achieved by a ridge that runs along the outer surface of the pedicle engagement device 20 that engages a groove within the internal passageway 46, 53 of the first and second screw capture elements 40, 50.

While the pedicle engagement devices 20 and first and second screw capture elements 40, 50 are described herein as being discrete elements that are in a rotational configuration, it is recognized that these elements may be monolithically integrated. In such an embodiment the pedicle engagement device 20 and second screw capture element 50 would be one monolithic device, and another pedicle engagement device 20 and the first screw capture element 40 would be another monolithic device.

Figure 5:
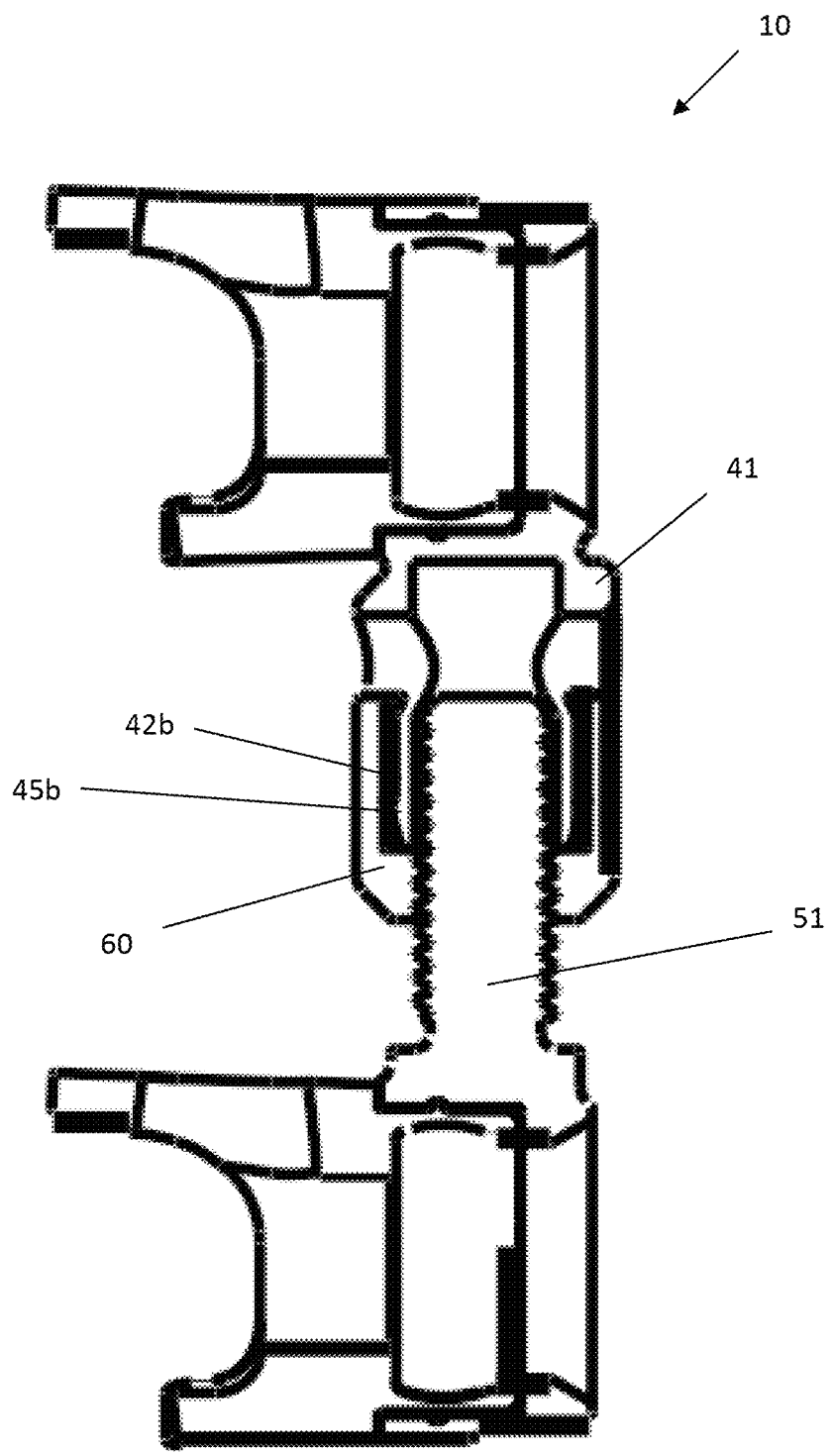
FIG. 5 is a cross-sectional view of the posterior fixation assembly of FIG. 1 along line A-A.

In accordance with one embodiment of the current invention, the expansion ring 60 may include one end that is internally threaded and another end that includes an array of teeth along the circumference. The expansion ring may also have geometry along the inner surface for engagement with flanges 45a, 45b, as seen in FIG. 5.

Figure 6:
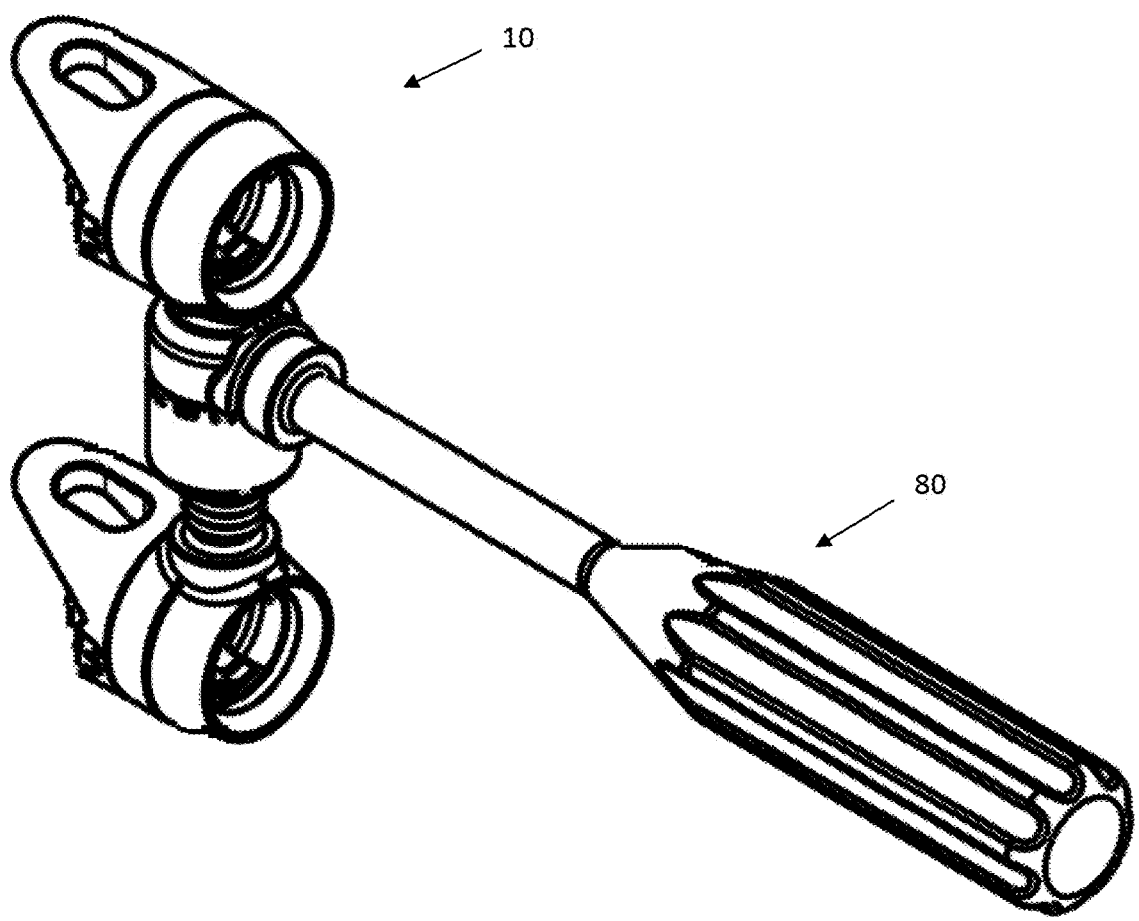
FIG. 6 is a perspective view of a driver engaging the posterior fixation assembly.

In assembling device 10, the spring arm extensions 42a, 42b of the first screw capture element 40 are inserted into the teeth-end of the expansion ring 60 until the flanges 45a, 45b engage with the internal geometry of the expansion ring 60. The spring-like action firmly seats the flanges 45a, 45b into place. This allows for rotation of the expansion ring 60 with respect to the first screw capture element 40, but prevents translational movement. The linking extension 41 preferably has an opening 44 in the sidewall to expose the teeth of the expansion ring. This exposure allows for engagement of a torque applying device, such as driver 80 as seen in FIG. 6, to the teeth 61 in order to apply a torque to the expansion ring 60.

The threaded extension 51 is screwed into the threaded-end of the expansion ring 60. Once the threaded extension 51 has traveled a certain distance into the expansion ring 60, the threaded extension 51 moves into the open area between the spring arm extensions 42a, 42b, thereby preventing the flanges 45a, 45b from disengaging the internal geometry of the expansion ring 60, as shown in FIG. 5. This configuration between the threaded extension 51, expansion ring 60, and spring arm extensions 42a, 42b allows for a torque applied to the expansion ring 60 via the teeth 61 to move the second screw capture element 50 closer or further away (depending upon the direction of the torque) from the first screw capture element 40, thus providing for compression and distraction of the vertebrae 90 attached to assembly 10.

In one exemplary embodiment of the posterior fixation assembly 10, where multilevel spinal distraction, compression and fixation is desired, the first screw capture element 40 that includes a single linking extension 41 is substituted by a first screw capture element 40 that includes two linking extensions 51. In this embodiment, an expansion ring 60 and first screw capture element 40 are assembled to each linking extension 41 as described above. This configuration would provide for two levels of fixation, or three vertebrae. Where more than two levels are desired, one of the second screw capture elements 50 that include a single threaded extension 51 may also be substituted for by a second screw capture element 50 that includes two threaded extensions 51. Thus, depending on the number of levels of vertebrae sought to be fused, there may be a first or second screw capture element 40, 50 that includes a single linking extension 41 or threaded extension 51, respectively, at the ends of the posterior fixation device 10, and a series of alternating first and second screw capture elements 40, 50 that include two linking extensions 41 and two threaded extensions 51, respectively, disposed therebetween.

Figure 7A:
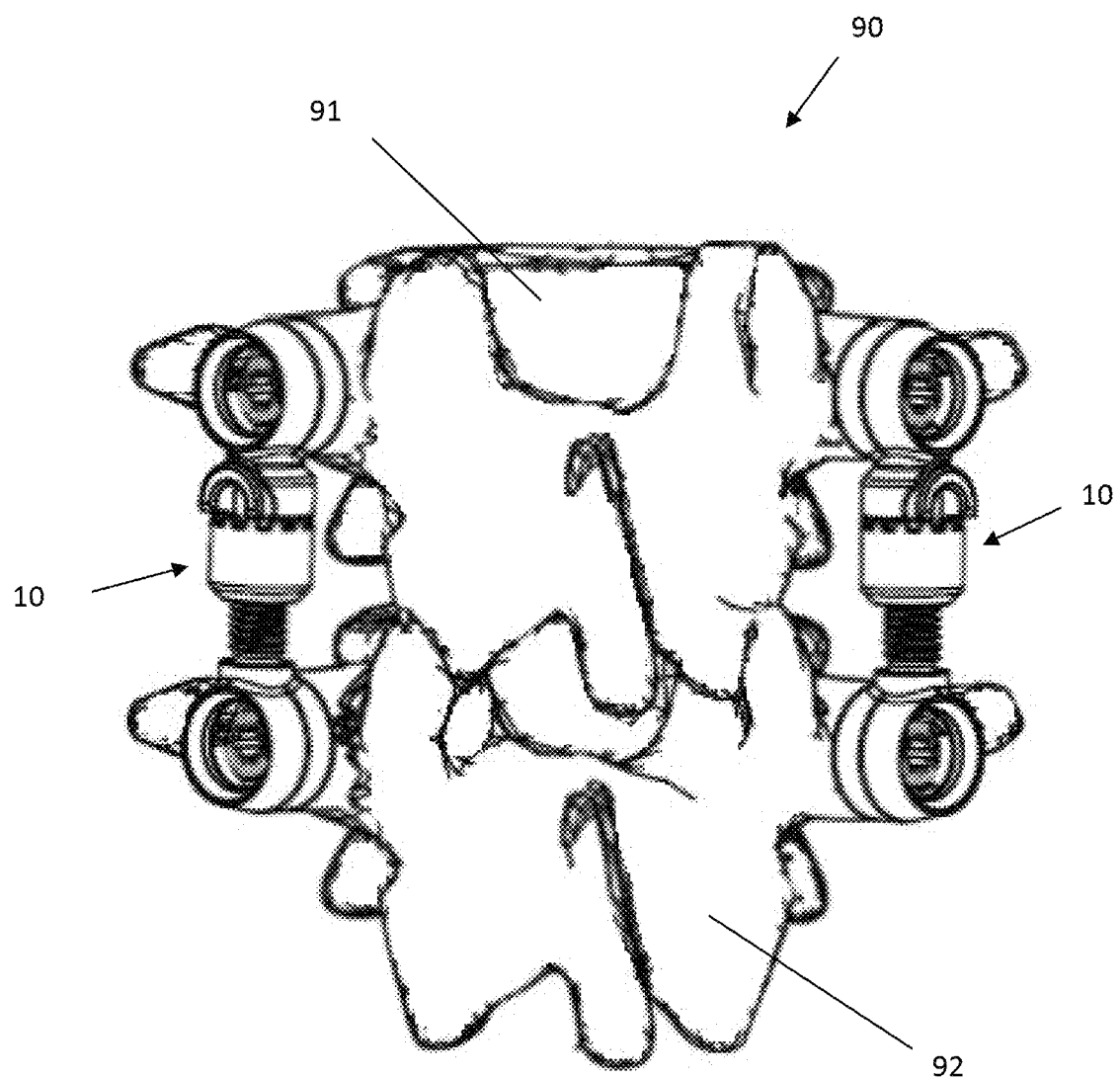
FIG. 7a is a rear view of two posterior fixation assemblies fixed onto the pedicles of vertebral bodies.
Figure 7B:
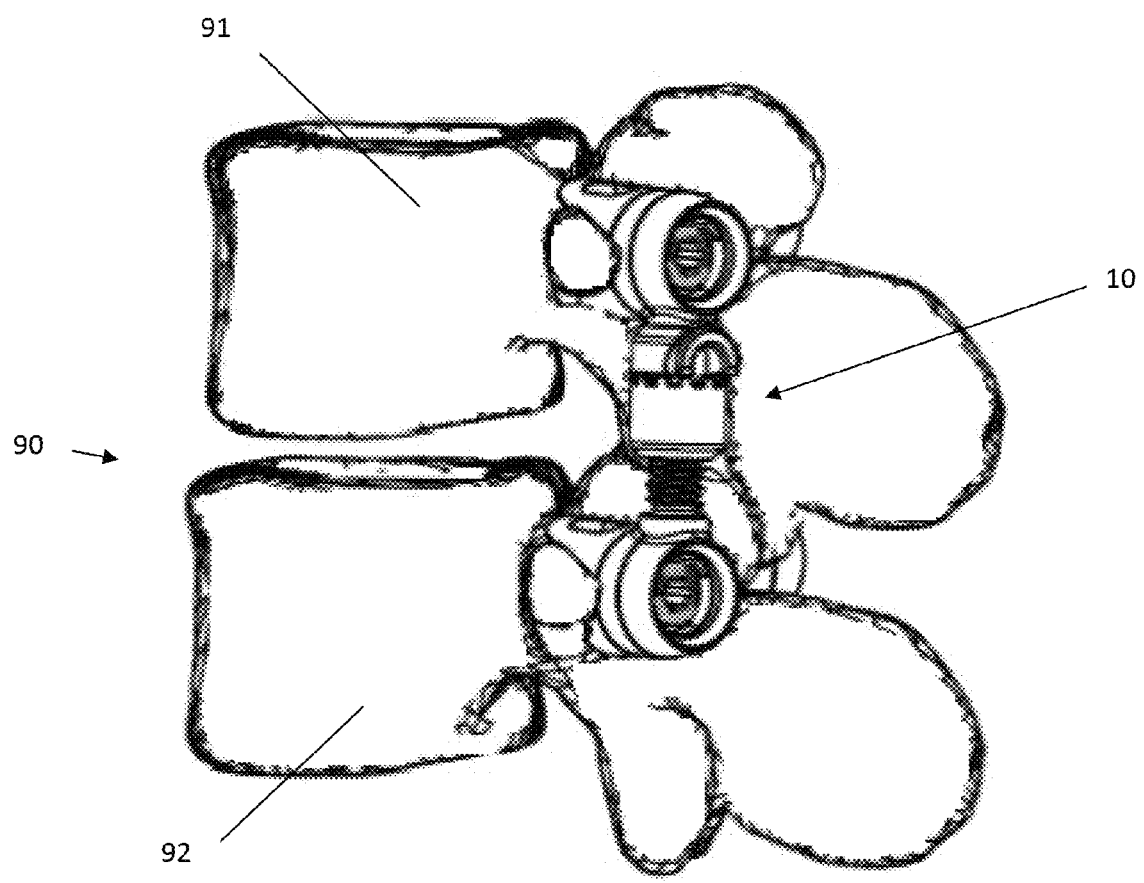
FIG. 7B is a side view of a posterior fixation assembly fixed onto the pedicles of vertebral bodies.
Figure 7C:
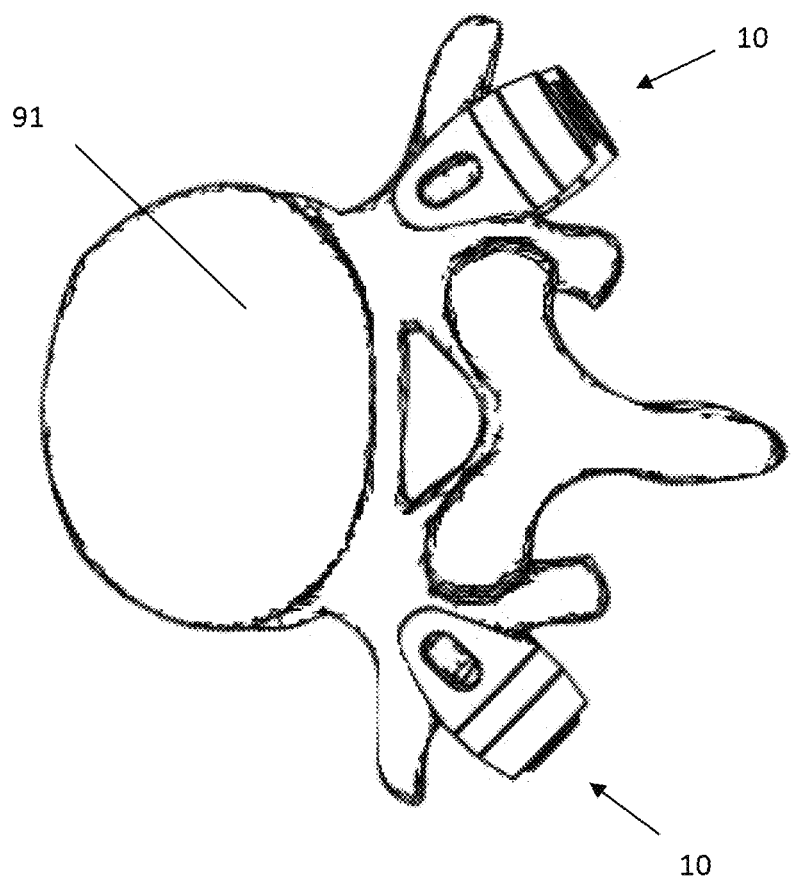
FIG. 7C is a top view of posterior fixation assemblies fixed onto the pedicles of vertebral bodies.

FIGS. 7A-C illustrate the posterior fixation assembly 10 in fixed engagement with pedicles of vertebral bodies, which may be achieved in any number of spinal interbody procedures including PLIF, TLIF, LLIF, and ALIF. As an example, where a transforaminal approach is taken and single level of vertebrae 90 is identified for fusion. An awl is hammered into the pedicles of the superior vertebra 91 and inferior vertebra 92 on one side of the spinous process. A hole is then drilled into the indentation created by the awl. A wire is then placed into the drilled holes and the first and second screw capture elements 40, 50 are routed over the respective wires. The pedicle engagement devices 20 of the first and second screw capture elements 40, 50 are initially seated onto the pedicles with the long extensions 21 oriented on the superior side of their respective pedicles. The pedicle engagement devices 20 may be rotated as needed in order to properly orient the long and short extensions 21, 22 with respect to the geometry of the pedicles. A cannulated screw may be passed over each wire through the respective first and second screw capture elements 40, 50. The cannulated screws may be fully seated by screwing the cannulated screws into the pedicles to the desired torque. As the screws move into a fully seated position, the serrations 24 of the pedicle engagement devices 20 are brought into engagement with bone to provide a secure attachment to the respective vertebra 91, 92. Once the screws are fully seated, a torque may be applied to the locking rings 70 via a torque applying device. As each locking ring 70 rotates, the non-uniform geometry of the pedicle engagement device forces the locking ring 70 to clamp down on the cannulated screw, thereby locking it into position to prohibit back-out. The driver 80 is then placed into interlocking engagement with the teeth 61 as seen in FIG. 6 and rotated, thus rotating the expansion ring 60 resulting in the distraction of the vertebral bodies.

The surgeon then prepares the disc space on the opposite side of the spinous process and inserts an intervertebral implant with bone graft into the space. Bone graft may be autologous, allograph, demineralized bone matrix (DBM), bone morphogenic protein (BMP) or any known combination of biologics. The driver 80 is then rotated in the opposite direction, thereby turning the expansion ring 60 in the opposite direction resulting in compression of the intervertebral implant and biologics. This compression also allows the surgeon to accurately set the desired angle of lordosis for the individual level of the spine. Achieving this angle may be further facilitated by use of a second screw capture element 50 that has an angled threaded extension 51, as described above. Further, the compression stimulates bone growth in accordance with Wolff's law.

Once the angle of lordosis is set, the surgeon then fixates another posterior fixation assembly 10 on the pedicles on the same side of the spinous process as the disc preparation was performed. This is achieved through the same steps as the first fixation by indenting with the awl, drilling the indentation, wiring the drilled hole, guiding the first and second screw captured devices 40, 50 and cannulated screws over the wire onto the pedicles, and seating the first and second screw capture features 40, 50; thereby achieving internal fixation and implantation.

In an example of a method of use in a PLIF procedure, the surgeon may fully seat a posterior fixation assembly 10 on both sides of the spinous process prior to preparation of the intervertebral space, as seen in FIG. 7A. Thus, after using a posterior approach and identifying the level for fusion, the surgeon hammers an awl into the pedicles of the superior vertebra 91 and inferior vertebra 92 on both sides of the spinous process. The surgeon then drills a hole at each indentation and wires the holes. The posterior fixation assemblies are routed over the wires via the first and second screw capture elements 40, 50. A cannulated screw is guided over the wires and screwed into the drill holes, thereby fixing the posterior fixation assemblies 10 onto the vertebrae 90. The locking rings 70 are clamped onto the screws. Screwdriver 80 may then be used is used to engage the teeth 61 of each posterior fixation assembly 10 and to rotate the expansion rings 60 resulting in distraction of the vertebral bodies, as seen in FIG. 7B. The surgeon then prepares the disc space between the respective posterior fixation assemblies 10 and the spinous processes. After implantation of the intervertebral implant, the screwdrivers 80 rotate the expansion rings 60 to provide for compression. Once implantation and supplemental fixation have been achieved, the patient is closed up.

In an ALIF procedure, the disc space is prepared and implanted first through an anterior approach. The patient is then rotated and a posterior fixation assembly 10 is then attached to the pedicles on each side of the spinous process with the same steps using the awl, drill, wires, and seating of the first and second capture features.

The posterior fixation assembly 10 may also be used for other applications such as corrective surgery for scoliosis. In a method of use for scoliosis, an initial surgery would be performed installing the posterior fixation assemblies 10, and then subsequent procedures would be performed wherein the surgeon may use the driver 80 to turn the expansion rings 60 to further expand or contract the disc spaces. Thus, over time, the incorrect curvature of the spine can be corrected.

In the above described methods of use, the posterior fixation assembly 10 may be fixed to the vertebrae 90 such that the first screw capture element 40 may be oriented superior or inferior to the second screw capture element 50. In other words, the first screw capture element 40 may be secured to the superior vertebra 91 while the second screw capture element 50 may be secured to the inferior vertebra 92, as shown in FIGS. 7A and 7B. Inversely, the second screw capture feature 50 may be secured to the superior vertebra 91 while the first screw capture element 40 may be secured to the inferior vertebra 92 (orientation not shown). Thus, the orientation of the posterior fixation assembly 10 may be flipped 180 degrees without altering its distraction, compression, and fixation capabilities.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A spinal surgery method comprising the steps of:
   mounting a posterior rod system to first and second vertebrae;
   distracting the first and second vertebrae by actuating the posterior rod system;
   inserting an intervertebral implant between the first and second vertebrae; and
   compressing the intervertebral implant between the first and second vertebrae by actuating the posterior rod system.

2. The method of claim 1, wherein mounting is performed intraoperatively and the posterior rod system remains mounted postoperatively.

3. The method of claim 1, further comprising:
   setting a desired angle of lordosis for the first and second vertebrae using the posterior rod system.

4. The method of claim 1, wherein distracting the first and second vertebrae includes engaging a driver to a rotating mechanism of the posterior rod system and rotating the rotating mechanism in a first direction.

5. The method of claim 4, wherein compressing the intervertebral implant between the first and second vertebrae includes engaging the rotating mechanism with the driver and rotating the rotating mechanism in a second direction.

6. The method of claim 4, wherein mounting the posterior rod system to the first and second vertebrae further includes:
   inserting a guidewire into each of the first and second vertebrae, and
   placing a screw capture element of the posterior rod system over each guidewire.

7. The method of claim 6, wherein mounting the posterior rod system to the first and second vertebrae includes:
   passing fasteners over each guidewire and through one of respective screw capture element, the fasteners being cannulated for receipt of the guidewire,
   driving the fasteners into the first and second vertebrae; and
   engaging locking rings coupled to each screw capture element with the fastener to restrict movement thereof.

8. The method of claim 1, further comprising:
   placing bone graft material into the intervertebral implant prior to implanting the intervertebral implant between the first and second vertebrae.

9. A method for fusing vertebral bodies comprising the steps of:
   accessing an intervertebral space between first and second vertebrae via a transforaminal approach;
   mounting a first engagement member to the first vertebra and a second engagement member to the second vertebra, the first and second engagement members being moveably connected;
   moving the first and second engagement members away from each other to distract the first and second vertebrae;
   inserting an intervertebral implant into the intervertebral space; and
   moving the first and second engagement members toward each other to compress the intervertebral implant between the first and second vertebrae.

10. The method of claim 9, wherein mounting includes inserting fasteners through the first and second engagement members into pedicles of the first and second vertebrae.

11. The method of claim 9, further comprising mounting third and fourth engagement members to the first and second vertebrae, respectively.

12. The method of claim 11, wherein the third and fourth engagement members are moveably connected and mounting the third and fourth engagement members to the first and second vertebrae.

13. The method of claim 12, inserting the intervertebral implant is performed through a transforaminal passage located at a first side of the spinous processes of the first and second vertebrae.

14. The method of claim 13, wherein the third and fourth engagement members are mounted to the first and second vertebrae on the first side of their respective spinous processes.

15. A method for fusing vertebral bodies comprising the steps of:
- accessing an intervertebral space between first and second vertebrae via a transforaminal approach;
- inserting a guidewire into a pedicle of each of the first and second vertebrae;
- placing a first engagement member over a guidewire extending from the first vertebra and a second engagement member over a guide wire extending from the second vertebra, the first and second engagement members being moveably connected via an actuation member and each having an opening for receipt of the guidewires;
- driving a fastener into each of the first and second vertebrae through the openings of the first and second engagement members to fix the first and second engagement members thereto;
- moving the first and second vertebrae away from each other by actuating the actuation member;
- inserting an intervertebral implant into the intervertebral space; and
- moving the first and second vertebrae toward each other by actuating the actuation member such that the intervertebral implant is compressed therebetween.

16. The method of claim 15, further comprising associating bone graft material with the intervertebral implant, the bone graft material being one of autologous bone, allograft bone, DBM, or BMP.

17. The method of claim 15, wherein:
- moving the first and second vertebrae away from each other includes engaging the actuation member with a driver and rotating the driver in the first direction, and
- moving the first and second vertebrae toward each other includes engaging the actuation member with the driver and rotating the driver in a second direction.

18. The method of claim 17, wherein the first and second directions are about an axis orthogonal to a rotational axis of the actuation member.

19. The method of claim 17, wherein engaging the actuation member with the driver includes intermeshing teeth of the driver with corresponding teeth of the actuation member.

20. The method of claim 15, wherein:
- inserting the intervertebral implant into the intervertebral space is performed at one side of the spinous processes of the first and second vertebrae, and
- driving the fasteners through the openings of the first and second engagement members is performed at an opposite side of the spinous processes of the first and second vertebrae.

* * * * *